United States Patent [19]

Smeltz

[11] 4,261,921
[45] Apr. 14, 1981

[54] PROCESS FOR PREPARATION OF A CRYSTALLINE INSECTICIDAL PYRETHROID ENANTIOMER PAIR

[75] Inventor: Leland A. Smeltz, Langhorne, Pa.

[73] Assignee: FMC Corporation, Philadelphia, Pa.

[21] Appl. No.: 46,147

[22] Filed: Jun. 6, 1979

[51] Int. Cl.³ .......................................... C07C 121/75
[52] U.S. Cl. .............................. 260/465 D; 424/304
[58] Field of Search ................... 260/465 D; 424/304

[56] References Cited

U.S. PATENT DOCUMENTS

| 4,024,163 | 5/1977 | Elliott et al. | 260/347.4 |
| 4,133,826 | 1/1979 | Warnant et al. | 260/465 D |
| 4,136,195 | 1/1979 | Warnant et al. | 424/304 |
| 4,151,195 | 4/1979 | Warnant et al. | 260/465 D |

FOREIGN PATENT DOCUMENTS 868034 12/1978 Belgium.
52-142046 11/1977 Japan.

Primary Examiner—Dolph H. Torrence
Attorney, Agent, or Firm—Robert L. Andersen; H. Robinson Ertelt; Robert M. Kennedy

[57] ABSTRACT

A crystalline, optically inactive compound comprising an equimolar mixture of the isomers (S)-(cyano) (3-phenoxyphenyl)methyl (1R,cis)-3-(2,2-dichloroethenyl)-2,2-dimethylcyclopropanecarboxylate and (R)-(cyano)-(3-phenoxyphenyl)-methyl (1S,cis)-3-(2,2-dichloroethenyl)-2,2-dimethylcyclopropanecarboxylate, its preparation by a cyclic crystallization/equilibration process, and its utility as an insecticide are described and exemplified.

1 Claim, No Drawings

PROCESS FOR PREPARATION OF A CRYSTALLINE INSECTICIDAL PYRETHROID ENANTIOMER PAIR

The present invention relates to an insecticidal pyrethroid and a method for preparation. More particularly the invention relates to the pyrethroid, (cyano)(3-phenoxyphenyl)methyl 3-(2,2-dichloroethenyl)-2,2-dimethylcyclopropanecarboxylate. In accordance with one aspect of the present invention there is provided a crystalline, substantially equimolar mixture of (S)-(cyano)(3-phenoxyphenyl)methyl (1R,cis)-3-(2,2-dichloroethenyl)-2,2-dimethylcyclopropanecarboxylate (1R,cis-α-S isomer) and its enantiomer, (R)-(cyano)(3-phenoxyphenyl)methyl (1S,cis)-3-(2,2-dichloroethenyl)-2,2-dimethylcyclopropanecarboxylate (1S,cis-α-R isomer). In accordance with a second aspect of the invention there is provided a cyclic process for producing the claimed compound as a substantially optically inactive crystalline mixture of the 1R,cis-α-S and 1S,cis-α-R enantiomer pair having a high level of insecticidal activity.

U.S. Pat. No. 4,024,163 describes dihalovinylcyclopropanecarboxylates in general, including dibromo- and dichlorovinylcyclopropanecarboxylates, but not the isomeric mixture of this invention. That patent discloses separation of a single optically active isomer, (S)-(cyano)(3-phenoxyphenyl)methyl (1R,cis)-3-(2,2-dibromoethenyl)-2,2-dimethylcyclopropanecarboxylate from its 1R,cis-α-R diastereomer, by crystallizing a mixture of these two diastereomers from hexane. U.S. Pat. No. 4,133,826 discloses a comparable crystallization technique utilizing these isomers of the dibromo or dichloro compound, using isopropanol as a solvent.

U.S. Pat. No. 4,136,195 discloses the 1R,cis-α-S and 1R,cis-α-R isomers and mixtures of these two diastereomers of α-cyano-3-phenoxybenzyl 2,2-dimethyl-3R-(2,2-dichlorovinyl)cyclopropane-1R-carboxylate, but does not disclose the claimed isomeric mixture. This patent also teaches the 1R,cis-α-S isomer is the more active of the disclosed diastereomers, and that the 1R,cis-α-R and 1R,cis-α-S isomers may be separated chromatographically.

Japanese Kokai 52-142046 discloses the four isomers of the dl-trans and of the dl-cis forms of α-cyano-3-phenoxybenzyl 2,2-dimethyl-3-(2,2-dichlorovinyl)cyclopropanecarboxylate, the relationship of the four isomers in each group to each other, and the chromatographic separation of a crystalline pair of these isomers which is described as containing the "ineffective substances" (Relative effectiveness=3) from an oily mixture of isomers, described as the "effective substances" (Relative effectiveness=189).

U.S. Pat. Nos. 4,151,195 and 4,136,195 disclose equilibration between the 1R, cis-α-R and 1R,cis-α-S diastereomers of (cyano)(3-phenoxyphenyl)methyl 3-(2,2-dichloroethenyl)-2,2-dimethylcyclopropanecarboxylate by reacting the 1R,cis-α-R or 1R,cis-α-S diastereomer or a non-equimolar mixture thereof with a base in the presence of a solvent, and then recovering (a) the 1R,cis-α-S diastereomer (4,136,195) or (b) the equilibrated diastereomeric mixture of 1R,cis-α-R and 1R,cis-α-S isomers (4,151,195).

The racemic compound (cyano)(3-phenoxyphenyl)methyl (cis)-3-(2,2-dichloroethenyl)-2,2-dimethylcyclopropanecarboxylate has 4 isomers, designated I through IV:

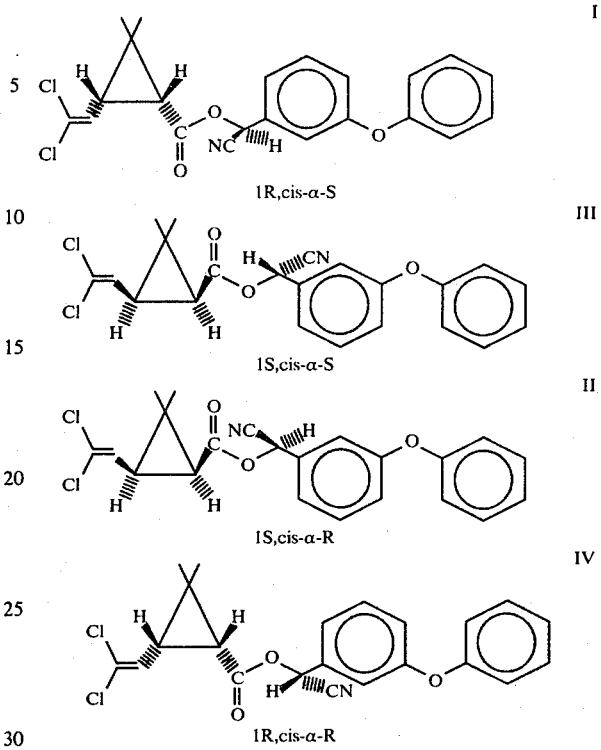

Throughout the specification the compound descriptions have been abbreviated as shown below structures I through IV. It will be understood that designations 1R,cis and/or 1S,cis refer to the spatial relationship of the hydrogen atoms at the 1 and 3 positions of the cyclopropane ring and the designations α-S and α-R refer to the spatial configuration of the cyano group on the α-carbon of the alcohol portion of the molecule. When or to the extent a specific isomeric designation is omitted from applicable nomenclature, the compound is a racemic mixture of the possible isomers.

The U.S. patents cited above deal with an optically active pair of diastereomers of 1R,cis configuration corresponding to formulae I and IV above, mixtures of I and IV, or the corresponding dibromoethenyl analog. Preparation of these diastereomeric pairs can only be achieved by use of a cyclopropanecarboxylic acid which is resolved into the 1R,cis configuration. Commercially this is undesirable, as resolution is an expensive, time-consuming step, and results in loss of approximately one-half of the racemic starting material due to unavailability of a commercially acceptable means for epimerization of the 1 and 3 positions of the cyclopropane ring. The Japanese Kokai, on the other hand, utilized the mixture of all four isomers and recovered the "ineffective substances" as a crystalline material and the "effective substances" as an oil.

In accordance with the present invention, there is provided a crystalline, optically inactive mixture comprising substantially equimolar amounts of the isomers (S)-(cyano)(3-phenoxyphenyl)methyl (1R,cis)-3-(2,2-dichloroethenyl)-2,2-dimethylcyclopropanecarboxylate and (R)-(cyano)(3-phenoxyphenyl)methyl (1S,cis)-3-(2,2-dichloroethenyl)-2,2-dimethylcyclopropanecarboxylate. The compound of the present invention is thus a crystalline racemic mixture of the enantiomer pair corresponding to compounds I and II above. This invention also provides an insecticidal composition comprising an insecticidal amount of this compound in admixture with a compatible, agriculturally acceptable diluent, carrier or adjuvant, including mixtures thereof, and a cyclic crystallization process for producing the compound.

The process aspect of this invention is a cyclic process starting with a mixture of the four isomers identified above (formulae I through IV), a racemic, substantially optically inactive mixture of the 1R,cis-α-S, 1S,cis-α-R, 1S,cis-α-S and 1R,cis-α-R isomers of (cyano)(3-phenoxyphenyl)methyl 3-(2,2-dichloroethenyl)-2,2-dimethylcyclopropanecarboxylate. In the crystallization step of the process that compound is treated with a non-polar solvent selected from the group consisting of an aliphatic or cycloaliphatic hydrocarbon of 5 to 8 carbon atoms to produce an optically inactive crystalline precipitate comprising substantially equimolar amounts of the 1R,cis-α-S, and 1S,cis-α-R isomers of (cyano)(3-phenoxyphenyl)methyl 3-(2,2-dichloroethenyl)-2,2-dimethylcyclopropanecarboxylate, and a mother liquor depleted of those isomers, but rich in the residual 1R,cis-α-R and 1S,cis-α-S isomers.

About 1 to 10 cc of solvent may be employed per gram of starting material, preferably about 2 to 5 cc/g, optionally 2 to 4 cc/g when the reaction is conducted at normal room temperature of 20°–25° C. The crystallization may, however, be conducted at a wide range of temperatures, for example in the range of −20° C. to 50° C. Nucleation begins shortly after the starting material is placed in the solvent and is promoted by stirring or other means of agitation. Crystallization is generally allowed to proceed over a period of 3 to about 64 hours, but is suitably complete in 4 to 24 hours, at which time the crystalline product is separated from the mother liquor by any suitable means, for example, filtration.

The residual 1R,cis-α-R and 1S,cis-α-S isomers are then separated from at least a portion of the solvent used in step 1, for example by evaporation of the solvent to produce a concentrate or an oily residue of the residual isomers. If substantially all the solvent is removed an oily residue of the residual isomers is produced.

The residual isomers are then reacted with a base selected from the group consisting of ammonia, lower alkyl primary, secondary, or tertiary amines in the presence of a solvent selected from the group consisting of aromatic hydrocarbons having 6 to 10 carbon atoms, for example benzene and toluene; saturated aliphatic or cycloaliphatic ethers having 4 carbon atoms, for example tetrahydrofuran, ethyl ether, or dioxane; aliphatic ketones having 2 to 4 carbon atoms; and chlorinated hydrocarbons having 2 to 4 carbon atoms. The solvent, of course, must be liquid at the temperature employed for the reaction.

This step of the reaction causes equilibration of the residual isomers to reproduce the starting isomeric mixture by epimerization of the cyano group about the α-carbon of the alcohol portion of the molecule, regenerating a racemic mixture of the 1R,cis-α-S, 1S,cis-α-R, 1R,cis-α R, and 1S,cis-α-S isomers. The conditions of time, temperature, and the like, are the same as those for the crystallization step.

Following the equilibration step, the solvent, and optionally the base, is removed to produce a concentrate or an oily racemic mixture of the starting isomers which are then returned to the crystallization step.

The following examples demonstrate the practice of the invention:

EXAMPLE I

Synthesis of (cyano)(3-phenoxyphenyl)methyl (cis)-3-(2,2-dichloroethenyl)-2,2-dimethylcyclopropanecarboxylate

A. Synthesis of (cyano)(3-phenoxyphenyl)-methanol as an intermediate

Into a flask were placed 755.7 g (2.5 moles) of the sodium salt of (hydroxy)(3-phenoxyphenyl)methanesulfonic acid, 237.6 g (1.25 moles) of sodium metabisulfite, and 2273 ml of water. The flask was cooled to 15° C. and a solution of 245.1 g (5.0 moles) of sodium cyanide in 302 ml of water was added dropwise. The reaction mixture was allowed to warm to room temperature, was stirred for 3 hours, then extracted three times with 800 ml of diethyl ether. The extract was washed once with 800 ml of a solution of 25% sodium metabisulfite and 1 N hydrochloric acid and twice with distilled water. After being dried over magnesium sulfate, the ether was evaporated, leaving a residue of 498.5 g of 94% (cyano)(3-phenoxyphenyl)methanol by gc analysis.

B. Synthesis of (cis)-3-(2,2-dichloroethenyl)-2,2-dimethylcyclopropanecarboxylic acid chloride as an intermediate In a flask were placed 400 g (1.913 moles) of cis-3-(2,2-dichloroethenyl)-2,2-dimethylcyclopropanecarboxylic acid and sufficient thionyl chloride to create a slurry. The remainder of the thionyl chloride (total used was 412.6 g (5.74 moles)) was added dropwise with stirring under a nitrogen blanket, and the reaction mixture was stirred at room temperature overnight. The crude product was distilled at 66°–67° C. at 66.7 Pa (0.5 mm of Hg) to produce 426.4 g of 98% (cis)-3-(2,2-dichloroethenyl)-2,2-dimethylcyclopropanecarboxylic acid chloride.

C. Synthesis of (cyano)(3-phenoxyphenyl)-methyl (cis)-3-(2,2-dichloroethenyl)-2,2-dimethylcyclopropanecarboxylate A mixture of 468.6 g (2.08 moles) (cyano)(3-phenoxyphenyl)methanol and 2500 ml toluene was placed in a flask and heated to 40° C. During an 80–85 minute period, 509 g (2.24 moles) of (cis)-3-(2,2-dichloroethenyl)-2,2-dimethylcyclopropanecarbonyl chloride prepared as described in Step B, and 186 g (2.35 moles) of pyridine were added under nitrogen. Upon completion of the addition, the reaction mixture was stirred 2.5 hours at 40° C. After cooling, the reaction mixture was washed successively with 1000 ml of water, 1000 ml of 1 N hydrochloric acid, 1000 ml of 1 N sodium hydroxide, twice with water, and once with an aqueous solution of sodium chloride. After being dried over magnesium sulfate, the solution was filtered through Celite and the solvent stripped using a rotary evaporator. Residual solvent was removed in a vacuum oven. A total of 918.3 g of 93.6% (cyano)(3-phenoxyphenyl)-methyl cis-3-(2,2-dichloroethenyl)-2,2-dimethylcyclopropanecarboxylate was obtained.

EXAMPLE II

Crystallization of a racemic mixture of (S)-(cyano)(3-phenoxyphenyl)methyl (1R,cis)-3-(2,2-dichloroethenyl)-2,2-dimethylcyclopropanecarboxylate and (R)-(cyano)(3-phenoxyphenyl)methyl (1S,cis)-3-(2,2-dichloroethenyl)-2,2-dimethylcyclopropanecarboxylate and base catalyzed diestereomeric equilibration of the residue Four samples of the product of Example 1.C, weighing 193.4 g, 182.9 g, 249.2 g, and 284.5 g, were dissolved in hexane, the first two in 550 ml of hexane, the third in 700 ml of hexane, and the fourth in 750 ml of hexane. After stirring overnight the precipitate was filtered off. From the first two samples a total of 96 g was isolated and from the third and fourth portions a total of 132 g was isolated. The combined solids were washed with 576 ml of hexane, giving 212.9 g of solid which had a melting point of 79°–81° C. Analysis by nmr confirmed that this solid was a racemic mixture of (S)-(cyano)(3-phenoxyphenyl)methyl (1R,cis)-3-(2,2-dichloroethenyl)-2,2-dimethylcyclopropanecarboxylate and (R)-(cyano)(3-phenoxyphenyl)methyl (1S,cis)-3-(2,2-dichloroethenyl)-2,2-dimethylcyclopropanecarboxylate. An additional 9.60 g of solid was recovered from the combined filtrates from the first and second samples after a second period of stirring. All filtrates and washings were combined and stripped of hexane using a rotary evaporator. The yellow, viscous oil that was recovered weighed 658.9 g. This oil was placed in a flask, and 1650 ml of toluene and 82 ml of triethylamine were added to the flask. After stirring for over 40 hours, the mixture was washed successively with 800 ml of 1 N hydrochloric acid, 800 ml of 1 N sodium hydroxide, once with water, and twice with a saturated aqueous solution of sodium chloride. The solution was dried over magnesium sulfate and then filtered through Celite. Removal of the toluene using a rotary evaporator left an amber, viscous oil weighing 648.9 g. Analysis by nmr showed that treatment with triethylamine had restored the ratio of isomers to that found in the product of Example I.

In accordance with the method aspect, the compounds of this invention are applied to the locus where insect control is desired, for example, to the insect itself or to the foliage or seeds of agricultural plants. The compounds are useful for the control of household, veterinary, and crop insects and may be applied as technical material or as a formulated product. Typical formulations include compositions of the active ingredient in combination with an agriculturally acceptable carrier or extender, optionally with an adjuvant such as a surface-active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of the active ingredient depending upon the particular agent used, the additives and carriers used, other active ingredients, and the desired mode of application. With due consideration of these factors, the active ingredient of a typical formulation may, for example, be suitably present at a concentration of about 0.1% up to about 95% by weight of the formulation. An agriculturally acceptable carrier or extender may comprise about 99.9% by weight to as low as about 5.0% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in the use dilution may be in the range of about 0.01 to about 10% by weight. Many variations of spraying, dusting, and controlled or slow release compositions of a type known in the art may be used by substituting or adding a compound of this invention into the compositions known or apparent to the art.

The compounds of this invention may be formulated and applied with other compatible active agents, including nematicides, insecticides, acaricides, fungicides, plant regulators, herbicides, fertilizers, synergists such as piperonyl butoxide, or a combination of these.

In applying these compounds, whether alone or with other agricultural chemicals, an effective insecticidal amount of the active ingredient must be applied. While the application rate will vary widely depending on the choice of compound, the formulation, mode of application, the plant species being protected, and the planting density, a suitable use rate may be in the range of 0.005 to 3 kg./hectare, preferably 0.01 to about 1 kg./hectare.

The compounds of this invention were tested for initial insecticidal activity as described below.

EXAMPLE III

Topical Application Test

The compound of this invention was tested for insecticidal activity by applying to the insect appropriate amounts of a toxicant solution containing 5 mg/ml of toxicant in acetone. The tests were read twenty-four hours after application of the toxicant solution and the percent kill determined. The commercial insecticide permethrin, 3-phenoxybenzyl (+) cis-trans-3-(2,2-dichlorovinyl)-2,2-dimethylcyclopropanecarboxylate, was used as the standard for comparison. Relative potency, based on a value of 1.0 for permethrin, was determined by comparing the $LD_{50}$ for the test compound with that for the standard. The insects employed include southern armyworm (*Spodoptera eridania* [Cram.]), cabbage looper (*Trichoplusia ni* [Hubner]), Mexican bean beetle (*Epilachna varivestis* Muls.), beet armyworm (*Spodoptera exigua* [Hubner]), milkweed bug (*Oncopeltus faciatus* [Dallas]), tobacco budworm (*Heliothis virescens* [Fabricius]), and corn earworm (*Heliothis zea* [Boddle]). The results of these tests are shown in the table below. In these tests the compound of the invention was substantially more active than permethrin.

| | Topical Application Test | | | | | | |
|---|---|---|---|---|---|---|---|
| | Insects[a] | | | | | | |
| | BAW | CEW | CL | MBB | MWB | SAW | TBW |
| $LD_{50}$[b] | 218.8 | 110.9 | 14.9 | 2.03 | 16.4 | 12.9–21.2 | 130.6–172.6 |
| Relative Po- | 5.1 | 2.5 | 9.0 | 7.2 | 37.6 | 1.0–1.5 | 4.2–6.1 |

| -continued | | | | | | | |
|---|---|---|---|---|---|---|---|
| Topical Application Test | | | | | | | |
| | Insects[a] | | | | | | |
| | BAW | CEW | CL | MBB | MWB | SAW | TBW |
| tency | | | | | | | |

[a]BAW = beet armyworm (*Spodoptera exigua*)
CEW = corn earworm (*Heliothis zea*)
CL = cabbage looper (*Trichoplusia ni*)
MBB = Mexican bean beetle (*Epilachna varivestis*)
MWB = milkweed bug (*Oncopeltus fasciatus*)
SAW = southern armyworm (*Spodoptera eridania*)
TBW = tobacco budworm (*Heliothis virescens*)
[b]ng/insect

EXAMPLE IV

Initial Contact (Foliar) Activity

The compound of the invention was dissolved in a solution of 90% water, 9.75% acetone, and 0.25% octylphenoxypolyethoxyethanol to give a solution having 512 ppm (w/w) active ingredient. Aliquots of this solution were diluted with an appropriate amount of water to provide solutions containing various concentrations of active ingredient. Test organisms and techniques were as follows: The activity against Mexican bean beetle (*Epilachna varivestis* Muls.) and southern armyworm (*Spodoptera eridania* [Cram.]) was evaluated by spraying the leaves of pinto bean plants with the test solution and infesting with 3rd instar larvae after the foliage had dried. The activity against the pea aphid (*Acyrthosiphon pisum* [Harris]) was evaluated on broad bean plants whose leaves were sprayed before infestation with adult aphids. To prevent escape of the insects from the test site, the complete test plant or the incised leaves were placed in capped paper cups. The tests were transferred to a holding room for an exposure period of 48 hours. At the end of this time the dead and living insects were counted, the $LD_{50}$ was calculated, and the potency relative to the commercial insecticide permethrin, 3-phenoxybenzyl (+) cis,trans-3-(2,2-dichloroethenyl)-2,2-dimethylcyclopropanecarboxylate determined. The $LC_{50}$ and relative potency are reported in the table below:

| Initial Contact (Foliar) Activity | | | |
|---|---|---|---|
| | Insects[a] | | |
| | MBB | PA | SAW |
| $LC_{50}$[b] | 1.62–1.86 | 1.39–21.15 | .22–.38 |
| Relative Potency | 5.3–8.8 | 2.5–9.8 | 9.8–16.1 |

[a]MBB = Mexican bean beetle (*Epilachna varivestis*)
PA = pea aphid (*Acyrthosiphon pisum*)
SAW = southern armyworm (*Spodoptera eridania*)
[b]concentration in parts per million

I claim:

1. A process for preparing a crystalline compound comprising a substantially equimolar mixture of the 1R,cis-α-S and 1S,cis-α-R isomers of (cyano) (3-phenoxyphenyl)methyl 3-(2,2-dichloroethenyl)-2,2-dimethylcyclopropanecarboxylate comprising:
   (a) treating racemic (cyano)(3-phenoxyphenyl)methyl (cis)-3-(2,2-dichloroethenyl)-2,2-dimethylcyclopropanecarboxylate with 1 to 10 cc per gram of a non-polar solvent selected from the group consisting of an aliphatic or cycloaliphatic hydrocarbon of 5 to 8 carbon atoms, then separating from the resulting mixture the solid phase consisting of said crystalline compound;
   (b) removing said solvent from the residual mother liquor to provide a concentrate rich in the residual 1S,cis-α-S and 1R,cis-α-R isomers;
   (c) treating the residual isomers with a base selected from the group consisting of lower alkyl, primary, secondary, or tertiary amines, ammonia or mixtures thereof in the presence of a solvent selected from a liquid aromatic hydrocarbon having 6 to 10 carbon atoms, a saturated aliphatic or cycloaliphatic ether having 4 carbon atoms, aliphatic ketones having 2 to 4 carbon atoms and chlorinated hydrocarbons having 2 to 4 carbon atoms, to provide a solution of the racemic compound (cyano)(3-phenoxyphenyl)methyl (cis)-3-(2,2-dichloroethenyl)-2,2-dimethylcyclopropanecarboxylate; then
   (d) removing said solvent from the solution, then treating said racemic compound in accordance with step (a).

* * * * *

UNITED STATES PATENT AND TRADEMARK OFFICE
CERTIFICATE OF CORRECTION

PATENT NO. : 4,261,921
DATED : 14 April 1981
INVENTOR(S) : Leland A. Smeltz

It is certified that error appears in the above-identified patent and that said Letters Patent are hereby corrected as shown below:

Column 6, line 44, "(+)" should read --(±)--. Colume 7, line 41, "(+)" should read --(±)--.

Signed and Sealed this

Thirtieth Day of November 1982

[SEAL]

Attest:

GERALD J. MOSSINGHOFF

Attesting Officer

Commissioner of Patents and Trademarks